United States Patent
Chiu et al.

[11] Patent Number: 5,282,254
[45] Date of Patent: Jan. 25, 1994

[54] METHOD FOR LOCATING AN EDGE PORTION OF AN APERTURE IN A FILTER MEMBER IN X-RAY FLUOROSCOPY APPARATUS

[75] Inventors: Ming-Yee Chiu, Princeton Junction, N.J.; David L. Wilson, Shaker Heights, Ohio

[73] Assignee: Siemens Corporate Research, Inc., Princeton, N.J.

[21] Appl. No.: 906,147

[22] Filed: Jun. 29, 1992

[51] Int. Cl.$^5$ ............................................. G06K 9/00
[52] U.S. Cl. ................................. 382/6; 364/413.13; 378/159; 382/22
[58] Field of Search .......................... 382/6, 22, 54; 364/413.13, 413.14, 413.15; 378/156, 158, 159, 99

[56] References Cited

U.S. PATENT DOCUMENTS

| | | | |
|---|---|---|---|
| 3,717,768 | 2/1973 | Edholm et al. | 378/159 |
| 5,086,478 | 2/1992 | Kelly-Mahaffey et al. | 382/22 |
| 5,209,232 | 5/1993 | Levene | 364/413.14 |

Primary Examiner—Leo H. Boudreau
Assistant Examiner—John B. Vigushin
Attorney, Agent, or Firm—Adel A. Ahmed

[57] ABSTRACT

The present invention is a method for locating an edge portion of an aperture in an X-ray filter member having at least one aperture formed therethrough, such that X-rays passing through the at least one aperture remain unattenuated and strike a subject body in a common region and wherein the X-rays passing through the filter member are attenuated and strike the subject body in a pattern that surrounds, and is adjacent to, the common region.

2 Claims, 7 Drawing Sheets

METHOD FOR LOCATING AN EDGE PORTION OF AN APERTURE IN A FILTER MEMBER IN X-RAY FLUOROSCOPY APPARATUS

FIELD OF THE INVENTION

The present invention relates to a method for locating an edge portion of an aperture in a filter member in X-ray fluoroscopy apparatus such as apparatus for reducing the dosage of X-ray radiation received by both a patient and medical personnel during an x-ray fluoroscopic procedure, and more particularly to such apparatus and methods that confine full X-ray dosage to a central area, compensating for the reduced X-ray dosage in the peripheral areas by computer imaging enhancement.

BACKGROUND OF THE INVENTION

Interventional radiology procedures are becoming more prevalent for the detection and treatment of many diseases and injuries. Often an interventional radiology procedure involves the viewing of a catheter, or needle, as it is directed into a desired position within the body. Catheter based medical procedures are commonplace and include such medical treatments as balloon angioplasty, laser ablation, the installation of stints and many other valuable treatments. In such medical procedures the progress of the catheter is typically monitored, within a patient's body, by an X-ray fluoroscope imaging system.

During a catheterization procedure, physicians and technicians need to position themselves next to the patient, in order to control the catheter. The overall X-ray exposure to such medical personnel can be higher than the X-ray exposure to the patient because medical personnel may do several X-ray fluoroscopic procedures in a single day and receive multiple dosages of X-ray radiation. For example, neuroangiographic procedures to repair an aneurysm or malformation may take as long as ten hours, during which the patient and physician are exposed to X-ray radiation much of the time. If the physician performs several such procedures a year, the physician quickly may exceed the recommended maximum dosage of radiation. The results of this potential for overexposure has been for highly trained physicians and other technical medical personnel to reduce their work load or to not wear their radiation monitor. Similarly, concern over overexposure may cause a physician to hurry a procedure, thus increasing the chances of making a mistake.

One way to reduce X-ray exposure from fluoroscopy is to use various shielding techniques. Staff can be protected with lead aprons, imaging chain canopies, lead gloves, and eye shields. Patients can be protected with gonad shields, etc. Many of these techniques are not often used because they interfere with the clinical procedure in one way or another.

In X-ray fluoroscopy it is well known that the dosage of the X-ray radiation is inversely proportional to the quantum noise in the viewed image. Prior art methods of X-ray dose reduction have addressed lowering the rate of dosage. For example, a nominal operational rate for X-ray fluoroscope is 30 frames/sec which may result in an exposure of approximately 10R/min skin dose. Prior art methods have attempted to reduce exposure by reducing the operational rate, for example, from 30 frames/sec. to 15 frames/sec. Such techniques have not been successful since a reduced frame rate necessitates an increased dosage rate per frame to minimize the quantum noise, the net result being no significant reduction in exposure.

Other techniques for reducing the dosage of X-ray radiation include operating the fluoroscopy imaging system in a zoom mode; in other words, limiting the X-ray radiation to a small region and electronically magnifying that region to form the entire viewed image Zoom mode imagery is not popular among some medical personnel because the zoomed image only permits a physician to view a small segment of a patient's body. Such a limited view makes it difficult for a physician to orient the placement of a catheter in a body, and prevents a physician from anticipating upcoming obstacles in the body until they appear in the zoomed image. In addition, in zoom mode, some X-ray systems increase the X-ray tube output dose such as to maintain a constant level of light output from the image intensifier. In that case, there is no dose saving to the patient.

It is therefore desirable to provide an apparatus and method for reducing X-ray radiation exposure to both patients and medical personnel without adversely affecting either the area of interest the X-ray fluoroscope procedure is being used to view, or the physician's ability to view the peripheral regions surrounding the area of interest.

Apparatus and a method for reducing the dosage of X-ray radiation incurred by a patient and medical personnel during a fluoroscopic procedure are disclosed in applicant's copending applications entitled APPARATUS AND METHOD FOR REDUCING X-RAY DOSAGE DURING A FLUOROSCOPIC PROCEDURE and METHOD FOR TRACKING A CATHETER PROBE DURING A FLUOROSCOPIC PROCEDURE, filed concurrently herewith and whereof the disclosures are herein incorporated by reference. During a fluoroscopic procedure X-rays are passed through a patient and are converted into a viewed image. Traditionally, the input X-ray beam is unattenuated across the entire field of view, even though it is herein recognized that, with some procedures, only a small area of the field of view actually requires high definition imaging The present invention includes a filter member that attenuates the X-ray radiation in areas of the field of view that are not of primary interest. With the filter member in place, a physician can still visualize the entire field of view for the purposes of orientation and placement, except that now the areas in the viewed image outside the point of interest are of lower quality. By attenuating the X-ray radiation in the areas outside the point of interest, the integrated-area dosage of X-rays is greatly reduced, as is the chance of overexposure to either the patient or the physician. There is an analogy to the retina fovea mechanism of the human eye to track an object of interest. Thus the concept is also referred to herein as an "X-ray fovea".

The attenuation of the X-ray radiation in selective areas changes in the brightness of the viewed image. Thus, the areas of the viewed image created by the attenuated X-rays are amplified to match the brightness of the viewed image created by the unattenuated X-rays. To prevent a distinct division of the viewed image between the areas formed by the attenuated and unattenuated X-rays, special image processing algorithms must be used. In addition, the filter member can have a varying transparency to X-rays, such that a smooth transition is made between the various regions of the viewed image and no discernable transition line appears in the image. In addition to compensating the brightness in the peripheral area, one may also introduce temporal or spatial filtering to reduce noise.

In one arrangement, the filter member is a substantially planar structure having a single aperture formed therethrough, the planar structure decreasing in thickness in the transition area such that the thickness of the planar structure is at a minimum at the edge of the aperture. Images of the filter plate or fovea collimator are obtained and algorithms on a workstation then find the center of the filter plate hole. Although the size of the filter plate hole changes with geometric magnification, the center remains fixed. Compensation of the image with regard to intensity and magnification changes requires finding the filter plate edge. Localization of the filter plate is also required for positioning the filter plate over an area of interest automatically by a systems controller.

SUMMARY OF THE INVENTION

In accordance with an aspect of the present invention, a method for locating an edge portion of an aperture in an X-ray filter member having at least one aperture formed therethrough, such that X-rays passing through the at least one aperture remain unattenuated and strike a subject body in a common region and wherein the X-rays passing through the filter member are attenuated and strike the subject body in a pattern that surrounds, and is adjacent to, the common region comprises recursively forming a gradient image of the common region; creating projections of the gradient image in the horizontal, vertical and two 45° directions, whereby peaks occur in the data of each projection where the projections pass tangentially near the gradient image and the distance between two peaks on a single projection represents a possible diameter of the gradient image; and matching peaks of the various projections to deduce the actual center and radius of the gradient image.

In accordance with another aspect of the invention, in an X-ray fluoroscopic apparatus for passing X-rays from an X-ray source arrangement through a subject body to an X-ray detector arrangement, including image processing arrangement coupled thereto for providing an image; a radiation reduction device comprising:

a controllable filter member arrangement being responsive to a control signal, and including a filter member being semi-transparent to X-rays and having at least one aperture formed therethrough, such that X-rays passing through the at least one aperture remain unattenuated and strike the subject body in a common region;

wherein the X-rays passing through the filter member are attenuated and strike the subject body in a pattern that surrounds, and is adjacent to, the common region;

a method for locating an edge portion of the at least one aperture comprises the following steps:

1. recursively forming a gradient image of the common region;
2. creating projections of the gradient image in the horizontal, vertical and two 45° directions, whereby peaks occur in the data of each projection where the projections pass tangentially near the gradient image and the distance between two peaks on a single projection represents a possible diameter of the gradient image;
3. matching peaks of the various projections to deduce the actual center and radius of the gradient image.

In accordance with another aspect of the invention, step 3 of the foregoing method for locating an edge portion comprises:

4. smoothing the data to eliminate smaller, inconsequential peaks in the data;
5. locating all pairs of peaks in the horizontal projection while ignoring all pairs of peaks which are separated by a distance that falls outside a range of possible diameters for the gradient image;
6. repeating for the vertical projection, as well as the two projections in the 45° direction, whereby the sampling distance along the two projections in the 45° directions is $1/\sqrt{2}$ of the horizontal and vertical sampling distance;
7. rescaling of the projection data relating to the two 45° directions prior to computation;
8. establishing for each projection a list of pairs of peaks that represent possible gradient pairs;
9. for each pair of projections, identifying all pairs of peaks in one projection that are separated by the same distance as any of the pairs of peaks in the other projection, whereby six listings are obtained of pairs of peaks that represent possible gradient images;
10. determining the center and inner radius for each possible gradient image 52 in the listings;
11. comparing the center and inner radius on each list to find a close match on another list; identifying a close match as probably being the gradient image.

In accordance with another aspect of the apparatus and method forming the context for the description of the invention, in an X-ray fluoroscopic apparatus for passing X-rays from an X-ray source to an X-ray detector, through a subject body; a radiation reduction device comprises:

a filter member, being semi-transparent to X-rays, and having at least one aperture formed therethrough, such that X-rays passing through the at least one aperture remain unattenuated and strike the subject body in a common region; and wherein the X-rays passing through the filter member are attenuated and strike the subject body in a pattern that surrounds, and is adjacent to, the common region In accordance with yet another aspect of the apparatus and method forming the context for the description of the invention, the filter member includes a transition area surrounding the at least one aperture, the transition area having an increased transparency to X-rays as the transition area approaches the at least one aperture.

In accordance with still another aspect of the apparatus and method forming the context for the description of the invention, the filter member is a substantially planar structure having a single aperture formed therethrough, the planar structure decreasing in thickness in the transition area such that the thickness of the planar structure is at a minimum at the edge of the aperture.

In accordance with a further aspect of the apparatus and method forming the context for the description of the invention, in an X-ray fluoroscopic procedure wherein an image is produced by passing X-ray radiation through a subject body a method of reducing the dosage of X-ray radiation striking the subject body, comprises the steps of:

selectively filtering the X-ray radiation such that attenuated and unattenuated X-ray radiation strike the subject body, the unattenuated X-ray radiation being confined to a predetermined common area surrounded by the attenuated X-ray radiation.

In accordance with still yet another aspect of the apparatus and method forming the context for the description of the invention, in an X-ray fluoroscopic procedure wherein a viewed image is produced, for monitoring the advancement of a medical instrument within a patient, by passing X-ray radiation through a patient; a method for reducing the dosage of X-ray radiation being exposed to the patient comprises the steps of:

selectively filtering the X-ray radiation such that attenuated and unattenuated X-ray radiation pass through the patient, the unattenuated X-ray radiation being confined to a common region;

calculating the size and position of the common region striking the patient; and altering the position of the common region to follow the advancement of the medical instrument, such that a point of interest on the medical instrument is viewed within the common region.

In accordance with another aspect of the apparatus and method forming the context for the description of the fluoroscopic apparatus for passing X-rays from an X-ray source arrangement through a subject body to an X-ray detector arrangement, including image processing arrangement coupled thereto; a radiation reduction device comprises:

a controllable filter member arrangement being responsive to a control signal, and including a filter member being semi-transparent to X-rays and having at least one aperture formed therethrough, such that X-rays passing through the at least one aperture remain unattenuated and strike the subject body in a common region;

wherein the X-rays passing through the filter member are attenuated and strike the subject body in a pattern that surrounds, and is adjacent to, the common region; and a control arrangement coupled to the X-ray source arrangement, to the image processing arrangement, and to the controllable filter member arrangement.

In accordance with yet another aspect of the apparatus and method forming the context for the description of the invention, the control arrangement provides the control signal to the controllable filter member arrangement for selectably placing the filter member in an operative mode.

In accordance with still yet another aspect of the apparatus and method forming the context for the description of the invention, in an X-ray fluoroscopic apparatus for passing X-rays from an X-ray source arrangement through a subject body to an X-ray detector arrangement, including image processing arrangement including image intensifier arrangement, coupled thereto for providing an image and including a radiation reduction device comprising:

a controllable filter member arrangement being responsive to a control signal, and including a filter member being semi-transparent to X-rays and having at least one aperture formed therethrough, such that X-rays passing through the at least one aperture remain unattenuated and strike the subject body in a common region;

wherein the X-rays passing through the filter member are attenuated and strike the subject body in a pattern that surrounds, and is adjacent to, the common region;

the control arrangement coupled to the X-ray source arrangement, to the image processing arrangement, and to the controllable filter member arrangement includes a method for tracking a catheter or probe, the catheter being characterized by at least some of the following characteristics A. relatively thin, less than 2mm, wire-like shape;
B. begins in periphery of the image;
C. has smooth edges;
D. does not bend much; and
X-ray dense as compared to the surround;

wherein the method comprises the following steps:
1. morphologically processing the image to enhance an image of the catheter;
   opening an input image, INPUT, with a flat, structuring element;
   subtracting the opened image from INPUT, to given ENHANCED;
2. threshold ENHANCED giving binary image, BINARY whereby the binary image contains silhouettes including a silhouette of the catheter;
3. analyzing regions or blobs, in BINARY to find the image of the catheter using properties of the catheter including the catheter being thin, relatively rigid, and X-ray dense;
   for each blob, make at least some of the following calculations:
   apply a thinning algorithm to obtain a medial axis;
   compute length of the medial axis, MEDIAL LENG;
   compute AREA and PERIMETER.
     DISTANCE_TO_PERIPHERY i (i=1,2), the distance of two endpoints of the medial axis to a periphery of the image intensifier;
     AREA_TO_PERIMETER, a ratio of the area to the perimeter;
     PERIMETER_TOMEDIAL_LENG, a ratio of the perimeter to the length of the medial axis;
     BENDING, an average local curvature of the medial axis;
   compute a mean intensity within the blob from ENHANCED;
   identify potential catheters by the following properties:
   a. One of the DISTANCE_TO_PERIPHERY measure should be close to zero;
   b. AREA_TO_PERIMETER should be close to half the width of the catheter;
   c. PERIMETER_TO_MEDIAL LENG should be close to 2.0;
   g. BENDING should be small;
   e. mean intensity should be within a predetermined value.
   for each potential blob, compute a score which is a function of measures identified above;
   select identification of the catheter as a blob from the set of potential catheters having the highest score;
4. finding the end of the catheter selected:
   the location of one endpoint of the medial axis farther away from the boundary is the end of the catheter selected; and
5. ending.

In accordance with still yet another aspect of the apparatus and method forming the context for the description of the invention, in an X-ray fluoroscopic apparatus for passing X-rays from an X-ray source arrangement through a subject body to an X-ray detector arrangement, including image processing arrangement including image intensifier arrangement, coupled thereto for providing an image and including a radiation reduction device comprising:

a controllable filter member arrangement being responsive to a control signal, and including a filter member being semi-transparent to X-rays and having at least one aperture formed therethrough, such that X-rays passing through the at least one aperture remain unattenuated and strike the subject body in a common region;

wherein the X-rays passing through the filter member are attenuated and strike the subject body in an attenuated pattern that surrounds, and is adjacent to, the common region;

control arrangement coupled to the X-ray source arrangement, to the image processing arrangement, and to the controllable filter member arrangement, including a method for correcting gray-scale values in the attenuated pattern region, comprising the following steps:

1. Entering a user-selected value for m in the equation for corrected values in a peripheral region, $G'_{p'p}$ $$G'_p = mG_p + b;$$

2. obtaining a value of b necessary to give similar gray values in a center region and the peripheral region, whereby pixel values are average in annuli in central and peripheral regions giving $\overline{G}_c$ and $\overline{G}_p$, respectively, deriving an appropriate value for b by computing $$b = G_c - m\ G_p; \text{and}$$

3. given b and m, calculating new pixel values in said peripheral region using the equation $G'_p = mG_p + b$.

In accordance with still yet another aspect of the apparatus and method forming the context for the description of the invention, in an X-ray fluoroscopic apparatus for passing X-rays from an X-ray source arrangement through a subject body to an X-ray detector arrangement, including image processing arrangement including image intensifier arrangement, coupled thereto for providing an image and including a radiation reduction device comprising:

a controllable filter member arrangement being responsive to a control signal, and including a filter member being semi-transparent to X-rays and having at least one aperture formed therethrough, such that X-rays passing through the at least one aperture remain unattenuated and strike the subject body in a common region; and wherein the X-rays passing through the filter member are attenuated and strike the subject body in an attenuated pattern that surrounds, and is adjacent to, the common region, with an annular transition region between the attenuated pattern and the common region;

a method for compensating for differences in image intensity in the transition region, comprises the following steps:

1. segmenting the transition region symmetrically into a plurality of arcuate segments;
2. obtaining the average overall intensity for a given arcuate segment over a range of radii, ranging from an inside boundary of the transition region to an outside boundary thereof;
3. calculating an intensity profile of the given arcuate segment; and
4. deriving from the intensity profile and applying to the given arcuate segment an intensity correction factor.

In accordance with a further, other aspect of the apparatus and method forming the context for the description of the invention, steps 3 and 4 of the foregoing method comprise:

a. calculating an average intensity of the given arcuate segment for the outside boundary of the transition region;
b. calculating an average intensity of the given arcuate segment 42 for the inside boundary of the transition region;
c. applying linear interpolation to the inside and outside boundary average intensity values to approximate what the average intensity ought to be for the full range of radii of the given arcuate segment;
d. determining the difference between the overall average intensity of the given arcuate segment and the interpolated intensity, at a given radius to create a correct compensation factor for the given arcuate segment;
e. adding the difference to the interpolated intensity and repeat for the entire range of radii; and
f. repeating the foregoing for each of the arcuate segments into which the transition region 32 has been divided.

BRIEF DESCRIPTION OF THE FIGURES

For a better understanding of the present invention, reference is made to the following description of an exemplary embodiment thereof, considered in conjunction with the accompanying drawings, in which.

DETAILED DESCRIPTION OF THE PREFERRED EMBODIMENTS

Figure 1:
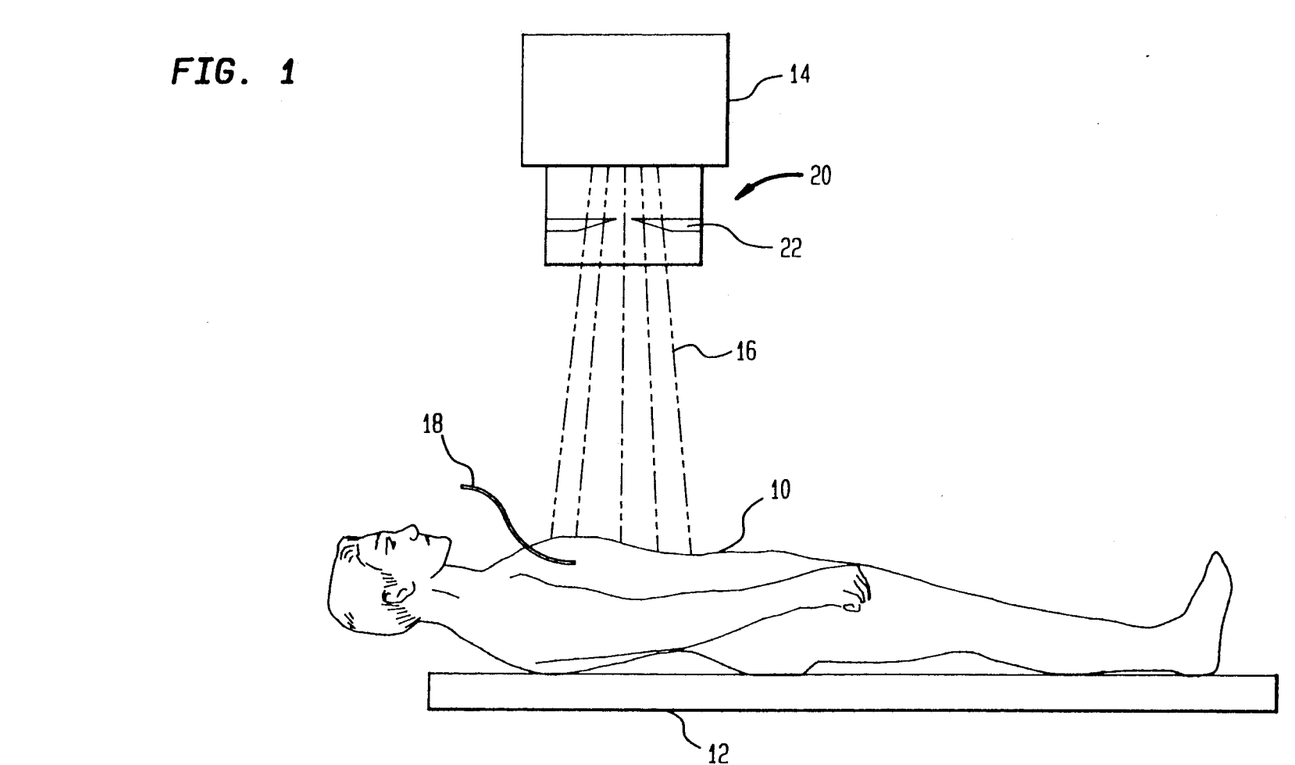
FIG. 1 is a general schematic illustration of one embodiment of the apparatus and method forming the context for the description of the present invention, showing a filter member being used in conjunction with an X-ray fluoroscopy apparatus.

Referring to FIG. 1 there is shown a patient 10 undergoing an X-ray fluoroscopic procedure. Below the patient 10 is positioned a fluoroscopic image intensifier assembly 12, and above the patient 10 is an X-ray source 14 that emits X-ray radiation 16. Typically, in a fluoroscopic procedure, the X-ray radiation 16 is directed to pass through the patient 10 and strikes the fluoroscopic image intensifier assembly 12. The fluoroscopic image intensifier assembly 12 converts the X-ray radiation 16 to a video signal which can be viewed on a CRT. The technology of X-ray fluoroscopy is well known and commonly used technology and, as such, need not be set forth herein in detail.

A common application of X-ray fluoroscopy is in monitoring the location of a catheter inside a body. Such catheters may be used for balloon angioplasty, laser ablation, or like procedures that are now often used in place of traditional invasive surgery. FIG. 1 shows a catheter 18 within a patient, and although the present invention may be used to detect guide wires, needles, tubes or other like devices in the body, the preferred embodiment to be described will reference a catheter based procedure.

Figure 2:
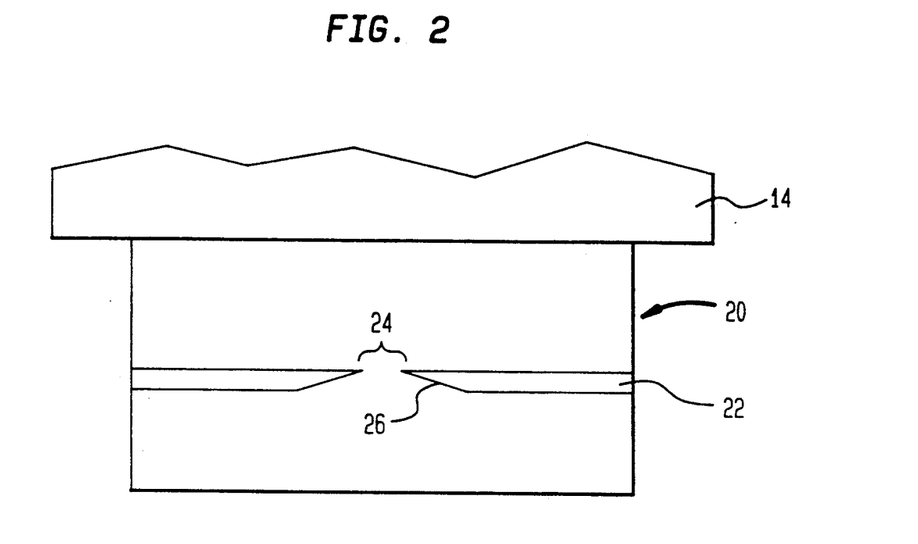
FIG. 2 is an enlarged view of the embodiment of the arrangement used in FIG. 1.

In FIG. 1 it can be seen that a collimator assembly 20 is placed between the X-ray source and the patient 10. An enlarged view of the collimator assembly 20 is shown in FIG. 2. As can be seen, the collimator assembly 20 includes a filter plate 22. The filter plate 22 is preferably fabricated from a material such as copper or brass that can be constructed in thin plates that are semi-transparent to X-ray radiation A small amount of aluminum, about 1 mm (or 0.40") or so should preferably be added so as to reduce K-edge radiation Centrally formed on the filter plate 22 is an aperture 24. The aperture 24 permits a small area of the X-ray radiation to pass from the X-ray source 14 to the patient 10 in an unattenuated form. Although one aperture 24 is shown, a plurality of apertures may be formed in a close pattern so that the X-ray radiation passing through each of the apertures would overlap in a substantially common region. Similarly, it should be understood that the filter plate 22 need not be formed from a single piece of material, but may be constructed as an iris assembly so that the size of the central aperture can be varied with either manual or electronic controls.

In the illustrated arrangement the filter plate 22 includes a tapered region 26 surrounding the central aperture 24. The thickness of the filter plate 22 changes from a maximum value, distal from the central aperture 24, to a minimum value bordering the central aperture 24. Since the filter plate 22 is made of material that is semi-transparent to X-ray radiation, the thickness of the filter plate 22 is directly related in an exponential fashion to the magnitude of its X-ray transparency. Consequently, the tapered region 26 varies in transparency from a minimum value, distal from the central aperture 24, to a maximum value bordering the central aperture 24. Although the tapered region 26 is shown, it should be understood that the varying transparency profile of the tapered region 26 can be reproduced by placing various spaced apertures in a uniformly thick filter plate. The apertures could become larger or more numerous as they approached the central aperture 24, thus producing the desired transparency profile. It should also be understood that although the tapered region 26, or its transparency profile equivalent is preferred, the present invention need not include such a construction. As such, the filter plate 22 would end abruptly at the edge of the central aperture 24.

Figure 3:
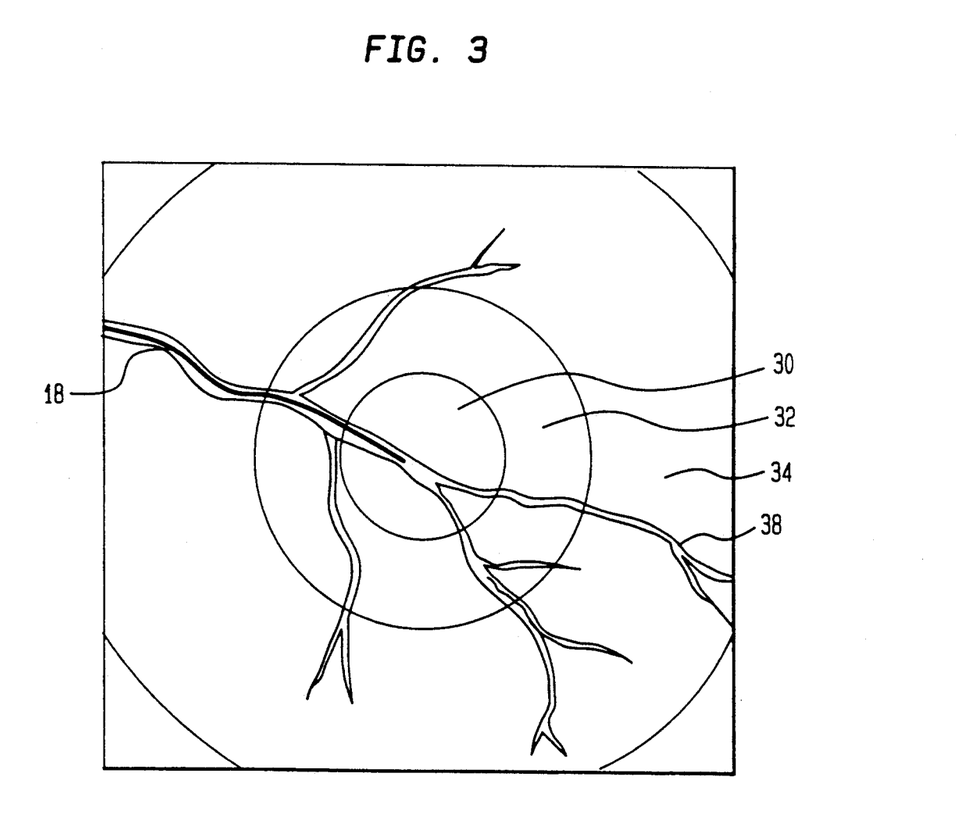
FIG. 3 is a view of an exemplary image provided by the X-ray fluoroscopy apparatus of FIG. 1.

In FIG. 3 there is shown the typical image that would be viewed from the X-ray fluoroscopy apparatus of FIGS. 1 and 2. As can be seen, three distinct circular regions are produced. The center region 30 is produced by X-ray radiation passing through the central aperture 24 of the filter plate 22. No energy is removed from the X-ray dosage in this center region 30; as such the center region 30 receives the most X-ray quanta and produces a low noise image. Surrounding the unfiltered center region 30 is the transition region 32. The transition region 32 can be created either by the X-ray radiation passing the tapered region 26 of the filter plate 22 or, if an abrupt filter is used, by the finite size of the X-ray source and the finite thickness of the abrupt filter. The tapered region 26 is thinnest at the edge of the central aperture 24 and increases in thickness as it travels away from the central aperture 24. Consequently, the X-ray radiation passing through the tapered region 26 is most intense, within the transition region 32, at the border with the center region 30. The intensity of X-ray radiation decreases within the transition region 32 as a function of the increase in the distance from the central region 30.

Surrounding the transition region 32 is the peripheral region 34. The image in the peripheral region 34 is produced by the X-ray radiation passing through the uniformly thick regions of the filter plate 22. Consequently, the image within the peripheral region 34 is formed with the most attenuated X-ray radiation. Since the image produced in the peripheral region 34 is the most attenuated, the peripheral region 34 receives the lowest amount of X-ray quanta. Consequently, the peripheral region 34 will produce an image with more noise than either the transition region 32 or the unattenuated center region 30.

Since the fluoroscopic image is quantum limited and approximately follows a Poisson distribution, a four times decrease in X-ray intensity (i.e. $T_x=0.25$) in the peripheral region, for example, would produce an image signal to noise ratio (SNR) reduction of two times, since the SNR is proportional to the square root of the X-ray intensity. Offsetting this effect is an increased lag in the dark regions of a video camera pickup tube. The increased lag results in a temporal filtering.

With the X-ray filter plate collimator, or fovea, present, the image quality in the center of the filter plate collimator hole is improved because of reduced X-ray scatter and reduced image intensifier veiling glare from the peripheral regions. This reduced scatter and glare results in a contrast improvement factor for low-contrast disks in the order of 1.5. Thus, with the filter plate collimator in place, the image quality in the hole area is actually improved. One can either use the system with the improved image quality, or reduce the grid ratio so as to maintain the same image quality with additionally reduced X-ray dose.

In FIG. 3 there is shown a catheter 18 being advanced through an artery 38. The area of interest to a physician in this application, would be the tip of the catheter 18. As such, the tip of the catheter 18 is positioned in the unattenuated center region 30 of the viewed image. The surrounding transition region 32 and peripheral region 34 are of less interest to a physician and are used primarily to give perspective and orientation to the physician. For example, a physician can view a large organ such as the heart in the peripheral region 34. The physician can then rationalize the position of the catheter tip to the heart without directly exposing the entire region to a full dosage of X-ray radiation. When the catheter 18 is in its desired position, the physician can then aim the center region 30 to cover any area of interest so as to obtain the best image possible.

By limiting the full X-ray dosage to a confined center region 30 a large reduction in X-ray radiation can be obtained for the patient and physician alike. As an illustration of the reduction in radiation obtained consider the following computed values. Assuming an X-ray fluoroscopy system emits radiation across an area (A), the total area-integrated entrance dosage ($D_m$) would be a product of the dosage per unit area ($D_x$) and the area (A). This is expressed as;

$$D_m = D_x \times A$$

If the present invention filter plate 22 is added to the X-ray fluoroscopy system, the total dosage $D_t$ is reduced to $$D_t = D_x T_x (A - A_h) + D_x A_h$$

where
$T_x$ is the percent transmittance of X-rays through the peripheral region; and
$A_h$ is the area of the central aperture 24.
The dose reduction is:

$$D_t/D_m = T_x (1 - A_h/A) + A_h/A$$

For a transmittance of 25% ($T_x = 0.25$), and a 5 cm diameter central aperture 24 in a 17 cm diameter field of view, the dose reduction is:

$$D_t/D_m = 0.31$$

which is equivalent to roughly one third of the X-ray dosage being used. Even larger entrance dose savings can be obtained.

At the periphery, the beam is hardened by the presence of the collimator. The harder, more penetrating, X-ray spectrum results in a further reduction of absorbed dose.

A problem that occurs with use of the present invention filter plate assembly is that the intensity of the viewed image is visibly different between the unattenuated center region 30, the transition region 32 and the peripheral region 34.

The variations in the intensity of the viewed image make the overall image difficult to read. To solve this problem, the pixels in the transitional region 32 and the peripheral region 34 are corrected to match the intensity of the center region 30. By correcting these regions, a uniform overall grey-level is maintained across the view image which results in a more readily comprehensible image.

The method for correcting the gray-scale values in the filter plate shadow follows.

Figure 4:
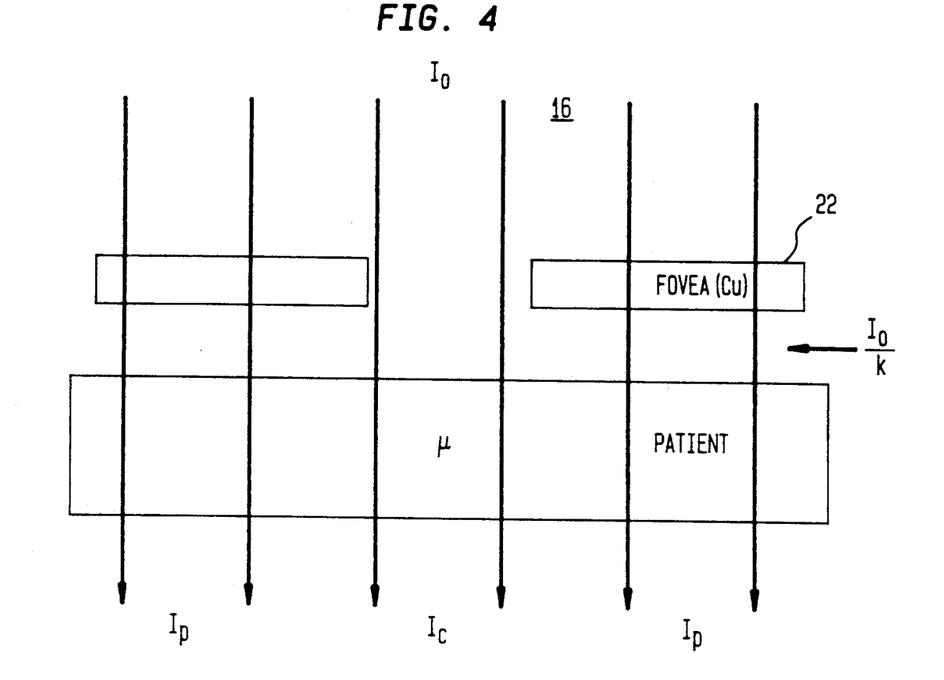
FIG. 4 shows an X-ray beam 16 impinging on the X-ray filter plate or "fovea" in accordance with the invention.

First, we will derive an equation that will be used to correct the image in the case of an X-ray image that has been acquired with log amplification. FIG. 4 shows the X-ray beam 16 impinging on the X-ray filter plate or "fovea" 22 and an object 10 being imaged. Filter plate 22 reduces the radiation intensity by a factor k which is equal to $$k = e^{-x\mu_{Cu}}.$$

The x-ray intensity exiting the object on either edge of the filter plate collimator is given below where $I_c$ and $I_p$ indicate the center and periphery of the image, respectively.

$$I_c = I_o e^{-\mu_1 t}$$

$$I_p = (I_o/K) e^{-\mu_2 t}$$

Because of beam hardening in the Cu filter plate, different effective absorption coefficients, $\mu_1$ and $\mu_2$, are used in the center and periphery. The thickness of the tissue being imaged is given by t. The digitized gray-scale value following log amplification is given below where A is a constant.

$$G = 1023 + A(\log I - \log I_o)$$

Substituting in the above equations we get the two equations below.

$$G_c = 1023 - A(\mu_1 t)$$

$$G_p = 1023 - A(\mu_2 t) - A(\log[k])$$

Eliminating t from the above equations gives $$G_c = 1023 + (\mu_1/\mu_2)G_p + (\mu_1/\mu_2)(A\log[k] - 1023)$$

Note that this is the equation of a straight line for variables $G_c$ and $G_p$. The slope and intercept are obvious from the equation and both are expected to depend upon the ratio of the $\mu$ values.

In practice, we use this result as follows. The equation for corrected values in the periphery, $G'_p$ is $$G'_p = mG_p + b \qquad \text{(Equation 2)}$$

where the slope and intercept parameters must be obtained. We allow the user to select a desirable value for m. Nominally a value of 1.2 is often acceptable. Higher and lower values of m result in contrast stretching and contraction, respectively. Given m, we then compute the b necessary to give similar gray values in the center and periphery. Pixel values are average in annuli in the center and periphery giving $\overline{G}_c$ and $\overline{G}_p$, respectively. An appropriate value for b is then given by $$b = \overline{G}_c - m\overline{G}_p.$$

Once these values are so obtained, image correction is done by simply applying Equation 2 to each pixel in the periphery region. This is the method for logarithmically acquired images. It is understood that fluoroscopic images may be obtained in a linear fashion and/or using other non-linear approaches such as to have a particular gamma characteristic. Straight-forward extension of the ideas proposed above result in correction equations for these other cases.

Figure 5:
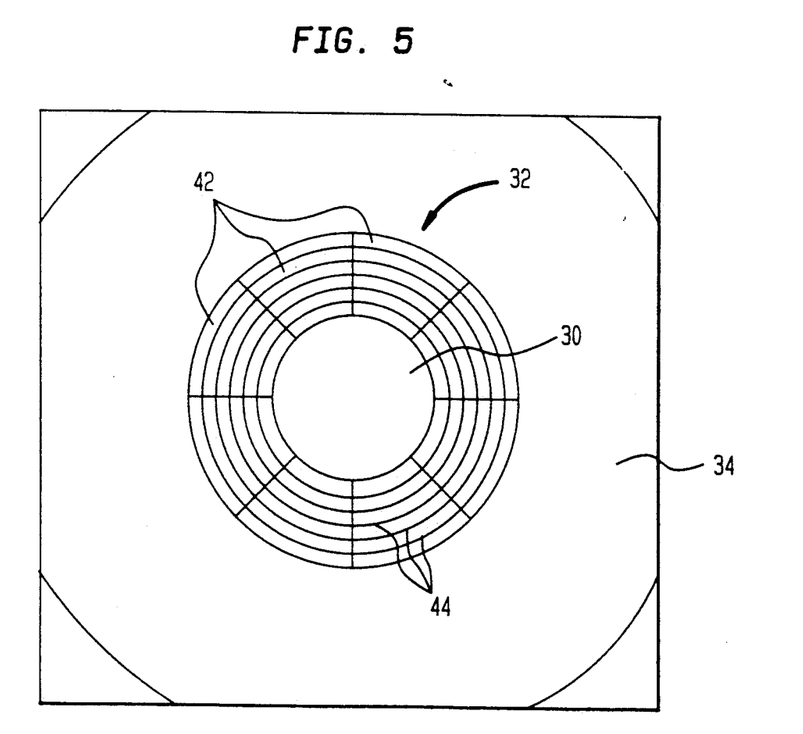
FIG. 5 is a view of an image produced by an X-ray fluoroscopy apparatus containing the present filter member, the transition zone of the image is sectioned to promote consideration and discussion.

In the transition region 32 the intensity of the image is somewhere between the higher intensity of the unattenuated center region 30 and the lower intensity of the peripheral region 34. The change in image intensity across the transition region 32 is not linear. As such, no simple constant can be added to the transitional region 32 to compensate for its decreased intensity Additionally, in actual use the transition region 32 is not entirely circular and may vary in its annular thickness. For example, the right side of the transition region 32 may be twelve pixels thick in the viewed image, while the left side of the transition region 32 may be sixteen pixels thick. To compensate for the varying thickness and intensity profile of each part of the transition region 32, the transition region 32 is symmetrically segmented into a plurality of arcuate segments. Referring to FIG. 5 a field of view showing an unattenuated center region 30, a transition region 32 and a peripheral region 34 are shown in a pattern similar to what was previously shown in FIG. 3. However, in FIG. 5 the transition region 32 has been selectively segmented into a plurality of arcuate segments 42. To correct the intensity of any one arcuate segment 42 to match the intensity of the center region 30, obviously the actual intensity of each arcuate segment must first be computed. To obtain the intensity for a given segment 42, first the average overall intensity of the arcuate segment 42 is found over a range of radii 44, ranging from the inside boundary of the transition region to the outside boundary By calculating the average overall intensity of an arcuate segment 42, the intensity profile of that particular segment 42 can be closely approximated, allowing a correction.

Obviously, there exists a difference between the average overall intensity of an arcuate segment 42 and the actual intensity of an arcuate segment 42 at a given radius. To determine the average intensity of an arcuate segment 42 at a given radius, the average intensity of the arcuate segment 42 is calculated for the outer boundary of the transition region 32. Similarly, the average intensity of the arcuate segment 42 is calculated for the inner boundary of the transition region 32. Once the inner boundary and outer boundary average intensity values are calculated, linear interpolation is used to approximate what the average intensity ought to be for the full range of radii 44.

To create the correct compensation factor for each arcuate segment 42, the difference between the overall average intensity of each arcuate segment 42 and the interpolated intensity, at a given radius, is determined. This difference is then added to the intensity and is repeated for the entire range of radii 44. This process is repeated for each segment 42 into which the transition region 32 has been divided. The final result is an image that is so well compensated that it is difficult to determine where the center region 30 and peripheral region 34 used to be, except for the inherent difference in signal-to-noise ratios. Since the transition region 32 is not easily discernable to the observer, the final viewed image is easily read and understood.

Figure 6:
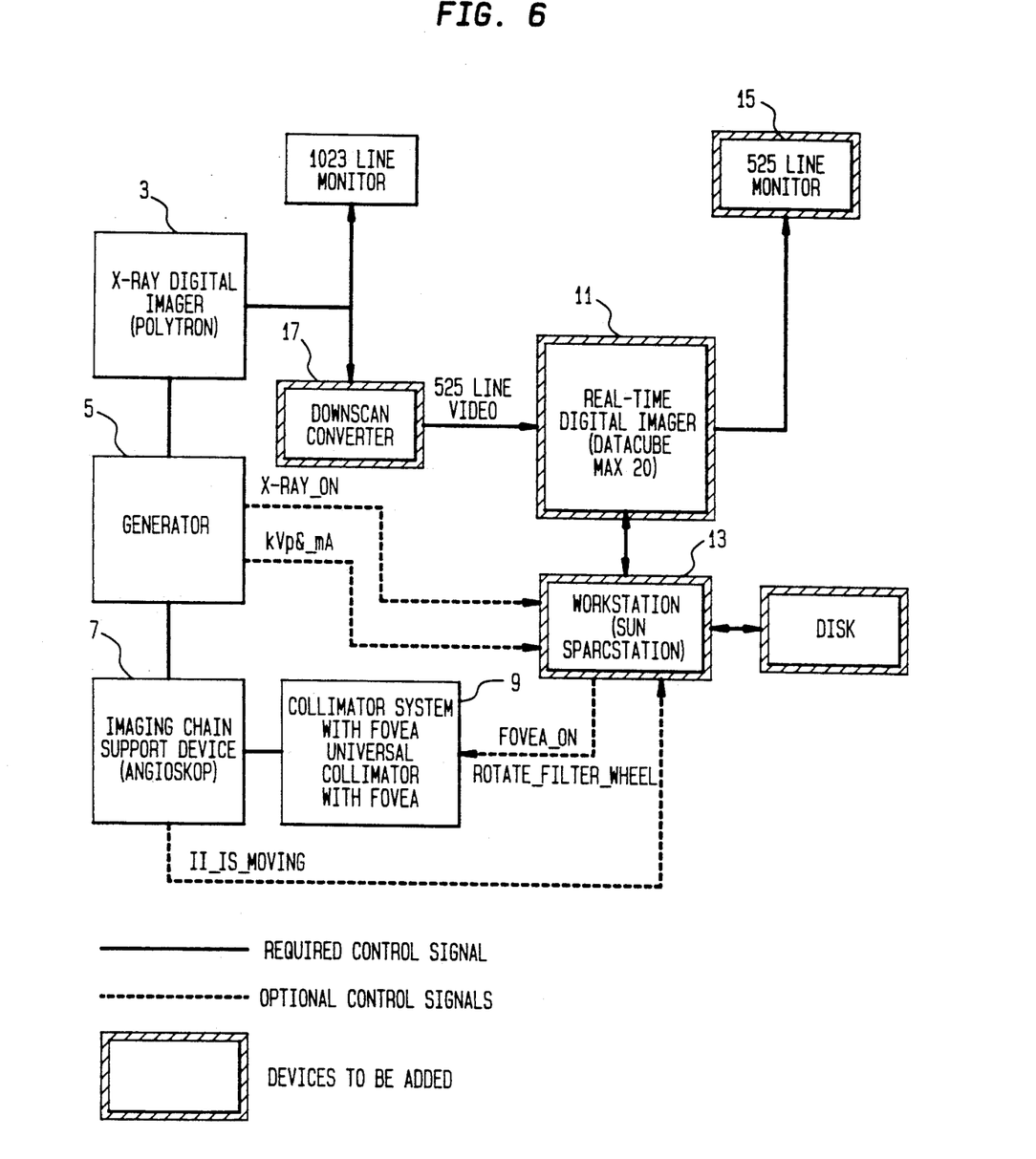
FIG. 6 shows an equipment diagram of a system in accordance with the apparatus and method forming the context for the description of the invention.

An equipment diagram of a system is shown in FIG. 6. The X-ray system (blocks without shading) is a conventional general angiography, or neuroangiography, system with a digital imaging device 3, such as a Siemens Polytron TM, an X-ray generator 5, and an imaging-chain support system 7 such as a C- or U-Arm that includes an image intensifier and video camera (not shown). The support system also has a collimation system 9 that allows one to rotate into place the filter plate collimator on demand. The X-ray filter plate components (shaded blocks) are a real-time image processing system 11, such as that manufactured by DataCube (Max 20); a workstation 13, such as a Sun Sparcstation; an image display monitor 15; and possibly a downscan converter 17 to convert from standard high resolution fluoro to RS170 video. Solid lines indicate general data paths. For example, the real-time image data begins at the video camera on the support device, is downscanned (optional), is digitized for filter plate shadow compensation, and is finally displayed on a low-resolution monitor. It is understood that this is a prototype system. In a commercial product implementation, the workstation tasks would be given to an imaging system computer and the imaging system would be a more specific hardware implementation that accepts high resolution video.

The X-ray system and prototype components are connected with several special signal lines (dashed lines). The X-ray_on signal is present to let the workstation know when it is appropriate to "grab" image frames for calculation of compensation parameters. Also, it may not be desirable to update the correction image while images are being taken. The signal kVp_&_mA, is presently primarily to let the workstation know when the patient has moved sufficiently to require a new X-ray dose. In this case, it may be desirable to make a new correction image. II_is_moving provides information that the image intensifier has moved closer, or further, from the X-ray tube, thereby changing the geometric magnification. Finally, fovea_on tells the support system to prepare for a filter plate acquisition by rotating the filter plate collimator into place.

Figure 7:
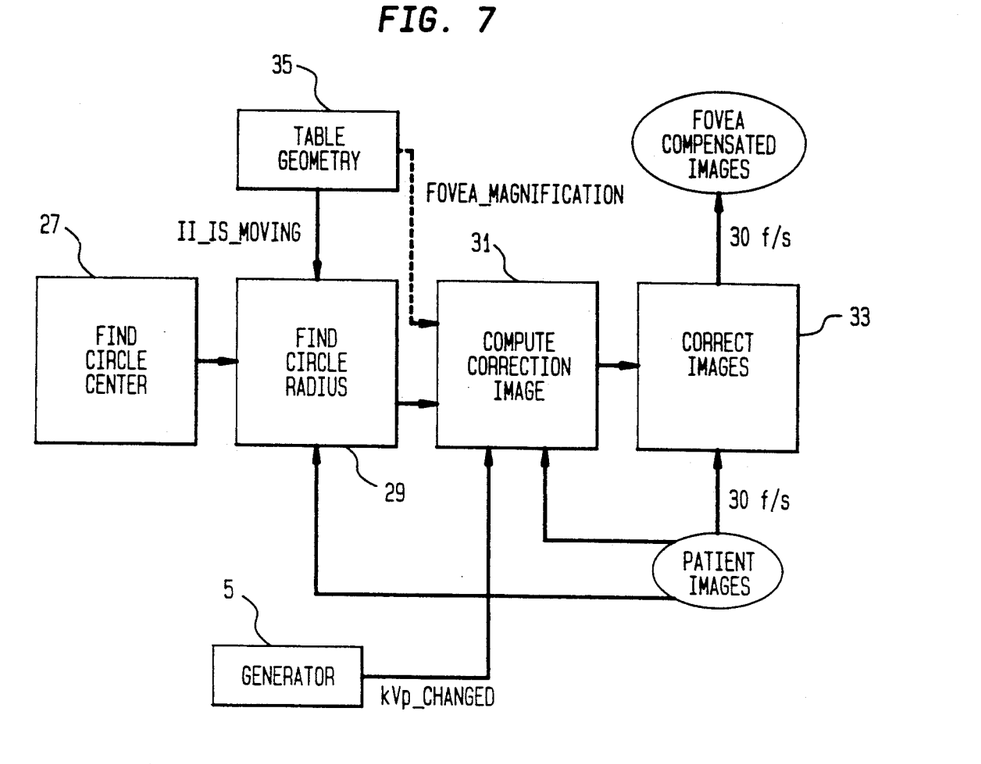
FIG. 7 shows a functional diagram of a prototype system in accordance with the apparatus and method forming the context for the description of the invention.

A functional diagram of a prototype system is shown in FIG. 7. On the right, is the real-time component (heavy black arrows) where patient images are corrected and displayed at 30 frames/sec. The four blocks placed along the center of the diagram (find circle center 27, and circle radius 29, compute correction image 31, and correct image 33) constitute the major functions of the system. center is run at the calibration time. Images of the filter plate or fovea collimator are obtained and algorithms on the workstation then find the center of the filter plate hole. Although the size of the filter plate hole changes with geometric magnification, the center remains fixed. Find circle radius is an algorithm running on the workstation that finds the radius of the collimator given the center of the circle. Compute correction image and correct image do just what their names imply.

The support geometry parameters 35 include II is moving and possibly fovea_magnification (optional). When the II has moved, we know that the filter plate magnification has changed. In this case, we can find the new filter plate edge. If accurate measurements of the geometry can be obtained, fovea_magnification can be used to compute a new correction image. Potentially, one might also combine these two functions. That is, one could use knowledge of an approximate fovea magnification to create search limits for and circle thereby making it faster and more robust.

The generator signal kvp_&_mA is monitored to determine when the X-ray tube output is changed in response to a change in X-ray absorption. This is a good indication of patient movement and is used to trigger compute correction image. Because of beam hardening, when the kVp changes, new correction image parameters are required.

As has been previously discussed, during a fluoroscopy procedure, X-ray radiation is detected and converted into an image signal by a fluoroscopic image intensifier assembly. The data contained by the image signal can be used to compute control commands that assist in the use of the present invention X-ray dosage reduction method. As has been explained, the present invention produces a center region 30 in the viewed image that corresponds to unattenuated X-rays passing through the patient As is well known, this unattenuated region has the most X-ray quanta and produces a low noise, high resolution image. Obviously, it is desirable to position this unattenuated center region over the area of interest the physician is concentrating on. One embodiment is to make the system track a feature of interest such as a catheter tip. Computations on the data contained in the image signal can be performed to isolate and track and area of interest This data can then be used to alter the position of the center region 30 so it follows, and remains above, the tracked area of interest.

Figure 8:
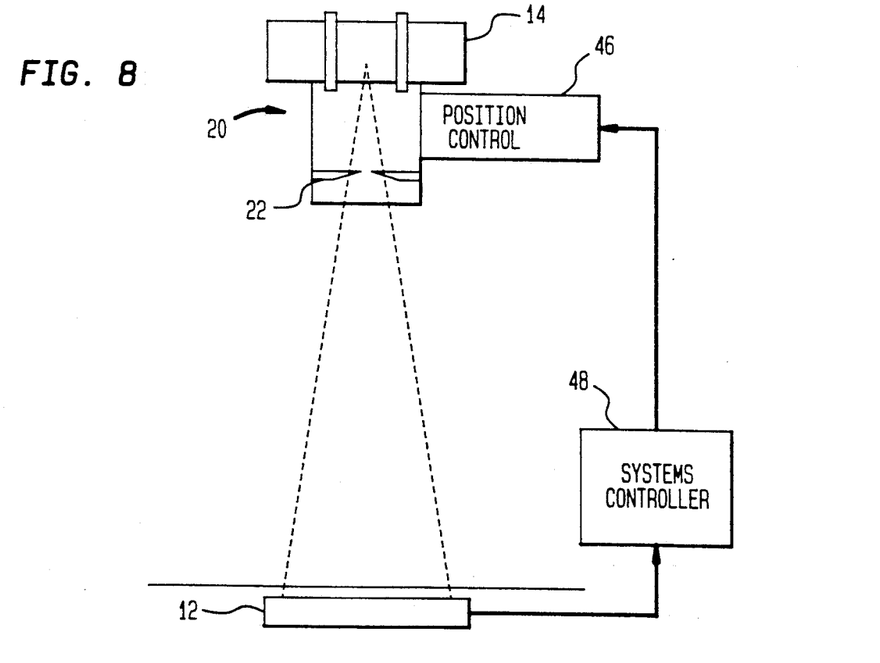
FIG. 8 is a general schematic of an X-ray fluoroscopy apparatus containing the present filter member and an automatic control system for selectively altering the position of the filter member.

Referring to FIG. 8 there is shown an embodiment of a fluoroscopy system wherein a position controller 46 is attached to the collimator assembly 20, and a systems controller 48 is coupled to the X-ray detector 12. The data contained within the image signal, generated by the X-ray detector 12 is computed to isolate a particular image in a patient's body, such as a catheter tip.

An embodiment for tracking follows

Reliable and fast determination of the tip location from the fluoro images using the digital image processing technique is required. As mentioned earlier, the fluoro images are noisy and the catheter is small. Thus, developing a robust tip tracking image processing algorithm is a major task. Furthermore, sometimes an exploratory guide wire may move ahead of the catheter and retract back later. Thus, the object to be tracked may change. If the circular filter plate region is large enough, the guided wire may still be within the central field of view. Another possibility is that the system must be switched between "catheter tracking" and "guide wire tracking" modes.

We will now describe a potential algorithm for finding the tip of the catheter. Features of the catheter to exploit in the algorithm include the following:
1. thin (<2mm), wire-like shape with roughly the same width
2. always begins in periphery of the image
3. smooth edges
4. doesn't bend much
5. X-ray dense as compared to the surround.

Steps in the algorithm are described below in pseudocode. For every few frames (say 3)
1. morphologically process the image to enhance the catheter.
   open the input image, INPUT, with a flat, say, 7×7 pixel structuring element subtract opened image from INPUT, to given ENHANCED
2. threshold ENHANCED giving binary image, BINARY. (The binary image should contain the silhouette of the catheter, as well as other objects.)
3. analyze blobs, or regions, in BINARY to find the catheter using the properties of the catheter mentioned above. There are many techniques described in the digital image processing textbooks to identify the catheter using shape descriptors. For example, see "Fundamentals of Digital Image Processing" by Anil Jain; 1989. One approach is described below:
   for each blob, make some of the following calculations
      apply the thinning algorithm (page 382 of the above-mentioned Jain's textbook) to obtain the medial axis.
      compute the length of the medial axis, MEDIAL_LENG
      compute the AREA and PERIMETER.
      DISTANCE_TO_PERIPHERY_i ($i=1,2$), the distance of two endpoints of the medial axis to the image intensifier periphery.
      AREA_TO_PERIMETER, the ratio of the area to the perimeter.
      PERIMETER_TO_MEDIAL_LENG, the ratio of the perimeter to the length of the medial axis.
      BENDING, the average local curvature of the medial axis.
      compute the mean intensity within the blob from ENHANCED.
   potential catheters must have the following properties:
      1. One of the DISTANCE_TO_PERIPHERY measure should be close to zero (begins in periphery).
      2. AREA_TO_PERIMETER should be close to half the width of the catheter (wire-like object).
      3. PERIMETER_TO_MEDIAL_LENG should be close to 2.0 (wire-like object).
      4. BENDING should be small (small bending).
      5. mean intensity should be within some values.
   for each potential blob, compute a score which is a function of the measures identified above.
   the catheter is the blob form the set of potential catheters having the ⓑhighest score.
4. find the end of the catheter
   the location of one endpoint of the medial axis farther away from the boundary is the end of the catheter.
End.

After the tip of the catheter is found, the displacement vector from the center of the hole to the tip is calculated. Command signals are then derived for moving the center of the collimator hole to the tip. The collimator should be a mechanized collimator such as the Universal Collimator TM currently sold by Siemens Medical Systems on various X-ray gantry systems such as the Multiskop and Angiostar TM.

In general, the invention should also allow other objects, such as needles, to be tracked as well.

As has been explained, compensation of the image requires finding the filter plate edge. One problem is that when the image intensifier is moved with respect to the X-ray source and filter plate collimator, the magnification of the filter plate shadow changes. Another complication is that many X-ray fluoroscopy units have zoom capabilities that alter the size of the image. Additionally, all patients are different, as are the areas of the patient being fluoroscopically examined. All these variables add up to make it difficult to accurately predict the size and shape of the center region 30, transition region 32 and peripheral region 34 comprising the viewed image. Since the various regions can probably not be predicted with sufficient accuracy, they must be measured in order to determine their size and location. Once located, the image can be corrected. Localization of the filter plate is also required for positioning the filter plate over an area of interest automatically by the systems controller.

Figure 9:
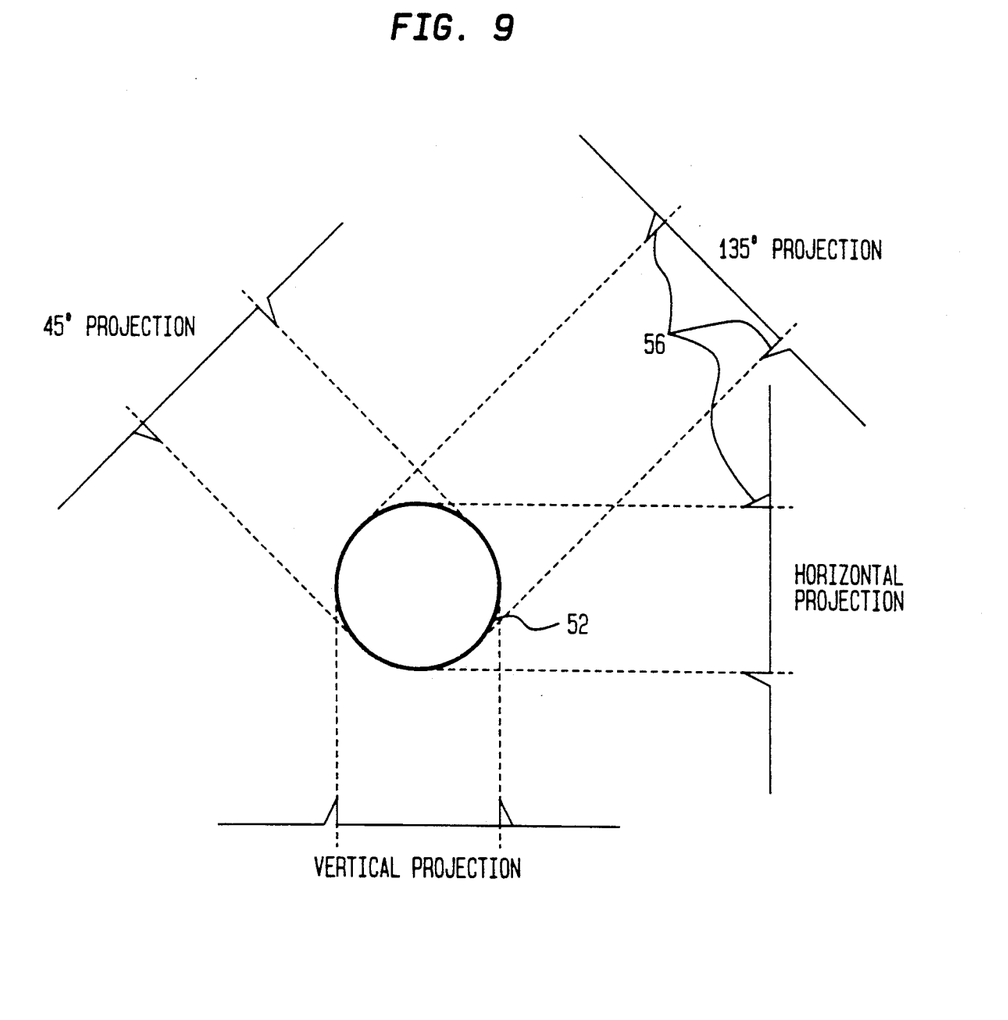
FIG. 9 is a view of the gradient image produced from a viewed image of an X-ray fluoroscopy apparatus containing the invention filter member.
Figure 10:
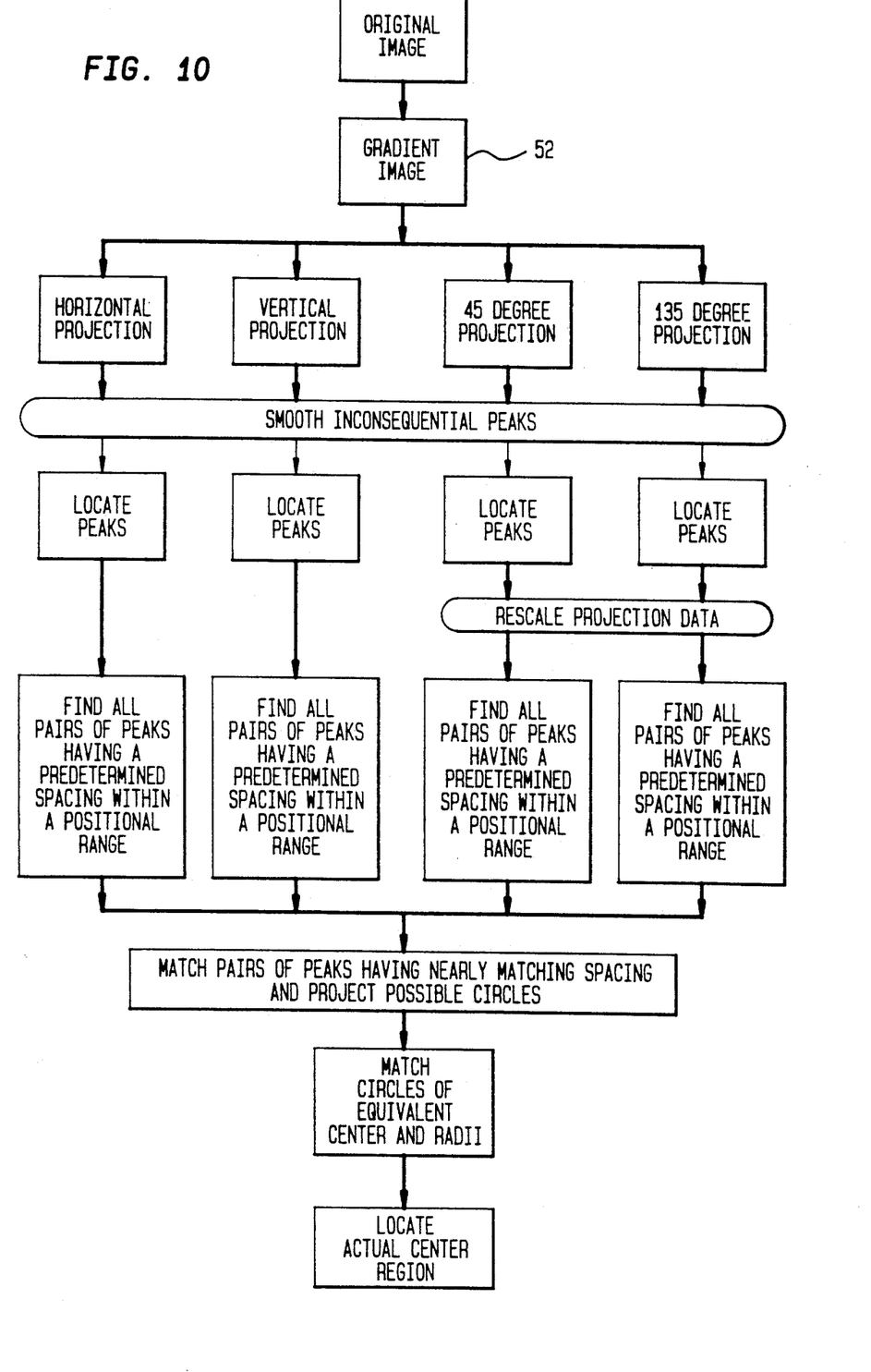
FIG. 10 is a flow diagram illustrating the method of determining the location of a gradient image on a field of view.

A particular method for finding the filter plate in accordance with the invention is now described. In order to locate the position and size of the center region 30 view image a gradient image is produced from the data of the image signal. Referring to FIGS. 9 and 10, a gradient image 52 of the center region 30 is recursively formed. Projections of the gradient image 52 are created in the horizontal, vertical and two 45° directions. Referring to the four projections, peaks 56 occur in the data of each projection where the projections pass tangentially near the gradient image 52. The distance between two peaks 56 on a single projection represent the possible diameter of the gradient image 52. By matching the peaks 56 of the various projections, it becomes possible to deduce the actual center and radius of the gradient image 52.

In a real image there will be many peaks 56 in each projection because the gradient has other structures in it besides the desired gradient image 52, so it may be needed that smoothing be performed first on the projection data to eliminate the smaller, inconsequential peaks in the projection data. However, there will still be other peaks in the projection data that do not necessarily correspond to peaks caused by the gradient image 52, so it is necessary to determine which sets of peaks correspond to the gradient image 52, and which peaks are caused by other structures. The key to peak correlation is finding those peaks 56 which correspond to the gradient image 52. First, all the pairs of peaks in the horizontal projection are found, ignoring all the pairs of peaks which are separated by a distance that falls outside a range of possible diameters for the gradient image 52 that is being searched for. This is repeated for the vertical projection, as well as two projections in the 45° direction. However, since the sampling distance along the 135° projection and the 45° projection is $1\sqrt{2}$ of the horizontal and vertical sampling distance, a rescaling of the projection data is needed prior to the computations.

Since the peaks 56 that correspond to a gradient image 52 are separated by the same distance in the projection data, the next step is to find all the pairs of peaks 56 in one projection that are separated by the same distance as any of the pairs of peaks 56 in the other projection. Then we have a list of pairs of peaks 56 that represent possible gradient images 52. For each possible gradient image 52 in this list, the center and inner radius can be determined. For four projections, we can have six pairs of pairs of possible gradient images 52. These lists of possible gradient images 52 (for the horizontal/vertical directions and the 45° directions) are then compared to find if there are any gradient images 52 on one list that match closely enough in center and radius to a gradient image 52 of the other list. If there are sufficient consistent matches (e.g., four matches out of six), the result is a good candidate for being the gradient image 52.

The above-described algorithm shown by FIG. 10 is merely exemplary and may be modified. For example, sometimes non-circular structures cause peaks that cause the algorithm to have "false circles", suggested circles that do not really fit the image data. One way to help prevent this would be to take the average intensity of the gradient image along each circle. Suggested circles that truly correspond to circles in the image data should have higher average intensities than the "false circles". Another method to improve robustness is to have the algorithm set strict conditions for determining whether a set of peaks corresponds to a circle, and then to relax those conditions if no circle is found. Finally, if the algorithm comes up with "false circles", it could take projections of the image data in other directions to confirm whether or not suggested circles do in fact correspond to circles in the image data.

With the center and radius of the gradient image 52 being known, the center and radius of the actual center region 30 of the viewed image is known. A computerized controller can then adjust the position of the collimator assembly 20 so that the center region 30 of the image is centrally positioned over an area of interest.

In the case of a fixed circular filter plate collimator the problem can be significantly reduced. The filter plate shadow is circular for all geometric magnifications, and the center of the circle should not move as the geometric magnification is changed. In this particular case, the algorithm above can be modified to allow the radius of the circle to change while constraining the circle center to remain unchanged. It is understood that there are a host of other algorithms that will find the filter plate edge.

It will be understood that the embodiment described herein is merely exemplary and that a person skilled in the art may make many variations and modifications without departing from the spirit and scope of the invention. More specifically, the central aperture formed in the filter plate of the present invention need not be round, but rather can be formed in any geometric shape. Similarly, the filter plate need not be tapered, thus eliminating the transition zone of the viewed image. All such variations and modifications are intended to be included within the scope of this invention as defined by the appended claims.

What is claimed is:

1. In an X-ray fluoroscopic apparatus for passing X-rays from an X-ray source means through a subject body to an X-ray detector means, including image processing means coupled thereto for providing an image; a radiation reduction device comprising:
   a controllable filter member means being responsive to a control signal, and including a filter member being semi-transparent to X-rays and having at least one aperture formed therethrough, such that X-rays passing through said at least one aperture remain unattenuated and strike said subject body in a common region;
   wherein the X-rays passing through said filter member are attenuated and strike said subject body in a pattern that surrounds, and is adjacent to, said common region;
   a method for locating an edge portion of said at least one aperture comprising the following steps:
   1. recursively forming a gradient image of said common region;
   2. creating projections of said gradient image in the horizontal, vertical and two 45° directions, whereby peaks occur in the data of each projection where said projections pass tangentially near said gradient image and the distance between two peaks on a single projection represents a possible diameter of said gradient image; and
   3. matching peaks of the various projections to deduce the actual center and radius of said gradient image.

2. A method for locating an edge portion in accordance with claim 1, wherein step 3 comprises:
   4. smoothing said data to eliminate smaller, inconsequential peaks in said data;
   5. locating all pairs of peaks in the horizontal projection while ignoring all pairs of peaks which are separated by a distance that falls outside a range of possible diameters for said gradient image;

6. repeating for said vertical projection, as well as said two projections in the 45° direction, whereby the sampling distance along the two projections in the 45° directions is $1\sqrt{2}$ of the horizontal and vertical sampling distance;
7. rescaling of the projection data relating to the two 45° directions prior to computation;
8. establishing for each projection a list of pairs of peaks that represent possible gradient pairs;
9. for each pair of projections, identifying all pairs of peaks in one projection that are separated by the same distance as any of the pairs of peaks in the other projection, whereby six listings are obtained of pairs of peaks that represent possible gradient images;
10. determining the center and inner radius for each possible gradient image 52 in said listings;
11. comparing the center and inner radius on each list to find a close match on another list; and
12. identifying a close match as probably being said gradient image.

* * * * *